(12) United States Patent
Robinson et al.

(10) Patent No.: US 8,273,020 B2
(45) Date of Patent: *Sep. 25, 2012

(54) METHOD AND SYSTEM FOR PROVIDING RULE BASED COGNITIVE STIMULATION TO A USER

(75) Inventors: Jerry Philip Robinson, Pacific Palisades, CA (US); Dan Michel, Los Angeles, CA (US); Melinda Wu, Los Angeles, CA (US)

(73) Assignee: Dakim, Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/317,529

(22) Filed: Oct. 20, 2011

(65) Prior Publication Data

US 2012/0077161 A1 Mar. 29, 2012

Related U.S. Application Data

(62) Division of application No. 11/607,781, filed on Dec. 2, 2006, now Pat. No. 8,083,675.

(60) Provisional application No. 60/748,326, filed on Dec. 8, 2005.

(51) Int. Cl.
*A61B 5/00* (2006.01)
(52) U.S. Cl. ......... 600/300; 600/301; 434/236; 128/898
(58) Field of Classification Search .................... None
See application file for complete search history.

(56) References Cited

U.S. PATENT DOCUMENTS

| | | | | |
|---|---|---|---|---|
| 5,911,581 A * | 6/1999 | Reynolds et al. | ............. | 434/236 |
| 6,164,975 A * | 12/2000 | Weingarden et al. | ......... | 434/322 |
| 6,280,198 B1 * | 8/2001 | Calhoun et al. | ............... | 434/236 |
| 6,435,878 B1 * | 8/2002 | Reynolds et al. | ............. | 434/236 |
| 6,533,584 B1 * | 3/2003 | Jenkins et al. | ................ | 434/236 |
| 6,626,676 B2 * | 9/2003 | Freer | ............................. | 434/236 |
| 6,652,283 B1 * | 11/2003 | Van Schaack et al. | ........ | 434/236 |
| 6,808,392 B1 * | 10/2004 | Walton | .......................... | 434/236 |
| 6,877,989 B2 * | 4/2005 | Embretson | ..................... | 434/236 |
| 6,921,268 B2 * | 7/2005 | Bruno et al. | .................. | 434/323 |
| 6,966,048 B2 * | 11/2005 | Bowers | ......................... | 717/101 |
| 7,186,116 B2 * | 3/2007 | Klingberg | ...................... | 434/236 |
| 7,294,107 B2 * | 11/2007 | Simon et al. | .................. | 600/300 |
| 7,309,315 B2 * | 12/2007 | Kullok et al. | ................. | 600/558 |
| 7,326,058 B2 * | 2/2008 | Abraham-Fuchs et al. | .. | 434/236 |
| 7,347,818 B2 * | 3/2008 | Simon | ........................... | 600/300 |
| 7,452,336 B2 * | 11/2008 | Thompson | ..................... | 600/558 |
| 7,756,827 B1 * | 7/2010 | Yung et al. | ..................... | 707/634 |
| 7,837,472 B1 * | 11/2010 | Elsmore et al. | ................ | 434/236 |
| 2002/0182574 A1 * | 12/2002 | Freer | ............................. | 434/236 |
| 2003/0129574 A1 * | 7/2003 | Ferriol et al. | ................. | 434/362 |
| 2004/0063081 A1 * | 4/2004 | Lipkins | .......................... | 434/236 |
| 2004/0128120 A1 * | 7/2004 | Coburn et al. | .................. | 703/26 |
| 2004/0137414 A1 * | 7/2004 | Ho et al. | ........................ | 434/236 |

(Continued)

*Primary Examiner* — Sam Yao
*Assistant Examiner* — Bobby Soriano
(74) *Attorney, Agent, or Firm* — Malcolm J. Romano

(57) ABSTRACT

A method and system for providing evolving, highly variable, long-term ongoing cognitive stimulation over a broad spectrum of cognitive domains. The user is presented with a series of entertaining audio/visual activities customized for the user, based on the user's life experience and cognitive level, each activity providing stimulation in one or more cognitive domains. The activities themselves and their level of challenge may change, in real time, over both the short- and the long term, varying in relation to current and historical user response patterns, creating an experience that remains engaging, with on-going use, over a period of months or years.

11 Claims, 20 Drawing Sheets

U.S. PATENT DOCUMENTS

| | | |
|---|---|---|
| 2005/0142523 A1* | 6/2005 | Martin ............................ 434/236 |
| 2005/0142524 A1* | 6/2005 | Simon et al. .................... 434/236 |
| 2005/0196734 A1* | 9/2005 | Poreh ............................. 434/236 |
| 2005/0244797 A9* | 11/2005 | Klingberg ...................... 434/236 |
| 2006/0003298 A1* | 1/2006 | Greenshpan et al. .......... 434/247 |
| 2006/0105307 A1* | 5/2006 | Goldman et al. .............. 434/236 |
| 2006/0115802 A1* | 6/2006 | Reynolds ....................... 434/236 |
| 2008/0206731 A1* | 8/2008 | Bastianova-Klett et al. . 434/322 |

* cited by examiner

Session Start

The session starts with the display of the logo, and the opening "bong" noise. This prompts the user to touch the screen on the green button that says "Press Here to Begin." A volume screen appears next, allowing the user to adjust the volume to their desired setting.

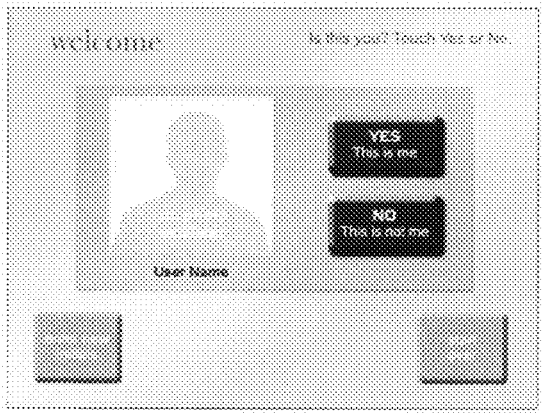

The system takes a photo of the user, and using a biometric id process attempts to identify the user using preloaded pictures, displays the picture to the user and asks for confirmation that the person in the photo is them.

FIGURE 10A

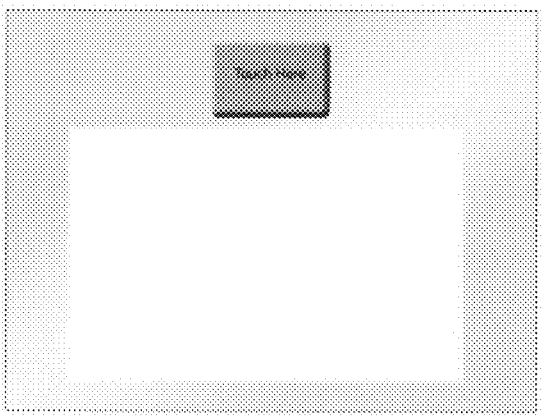

In the instance the system has trouble taking a valid picture, the system will prompt the user to press the "Touch Here" button and attempts to take another picture.

FIGURE 10B

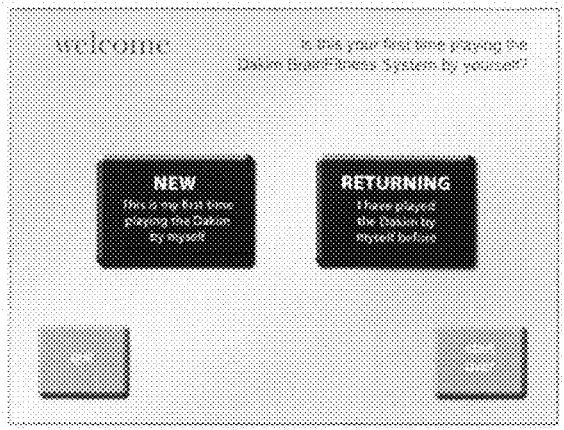

If the system is unable to identify the person through the photo process, the system asks the user whether or not this is the first time they've used the system by themselves before.

FIGURE 10C

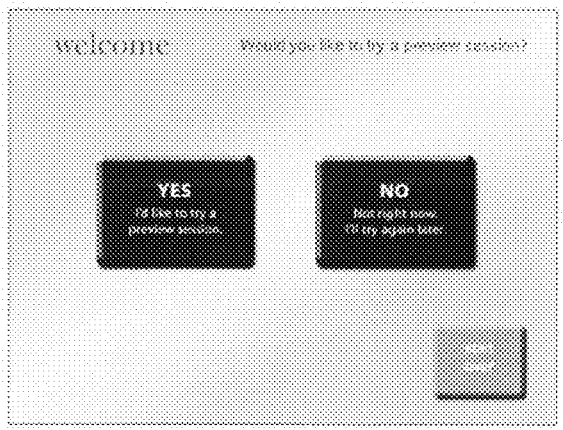

If the user answers that this is the first time they've been using the system by themselves, the system will present a keyboard for the user to type in their initials and identify themselves.

FIGURE 10D

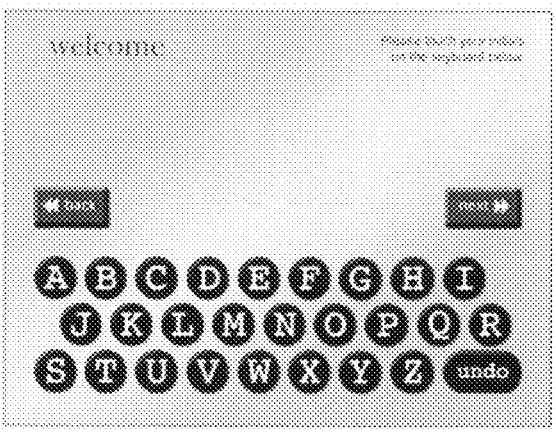

If the system is unable to identify the user, but the user has used the system before, the system will ask the user to try a demo session.

FIGURE 10E

The Announcer appears and greets the user. The Announcer instructs the user on how to interact with the system, by telling them to simply touch "various words and pictures in front of you." Then a short movie plays that displays various pictures and clips.

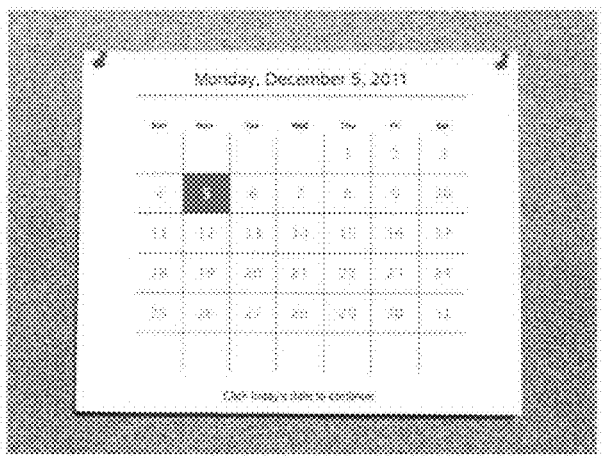

The system then shows an image of a calendar that highlights the day's date, and the Announcer announces the date, and then prompts the user to touch the calendar to continue.

FIGURE 10F

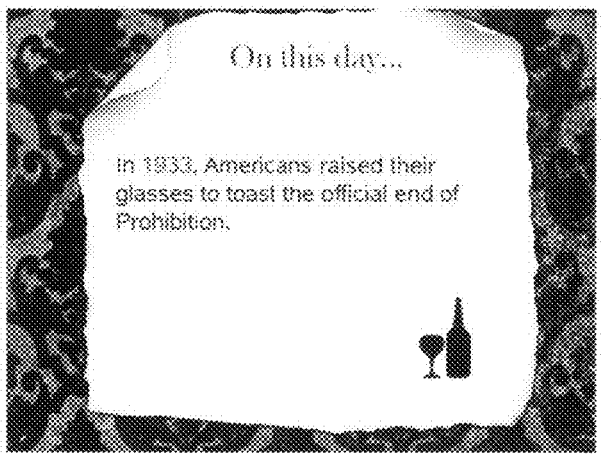

The system then will show an "On this Day" fact. In this case, it's August 7th, and the system details what occurred on August 7th in 1782, describing the introduction of the Purple Heart by then General George Washington.

FIGURE 10G

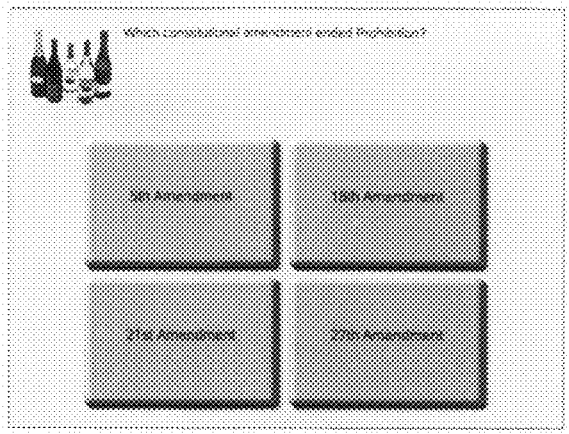

The system then asks a question related to the "On this Day" fact, in this case asking what the Purple Heart honors in the present day.

FIGURE 10H

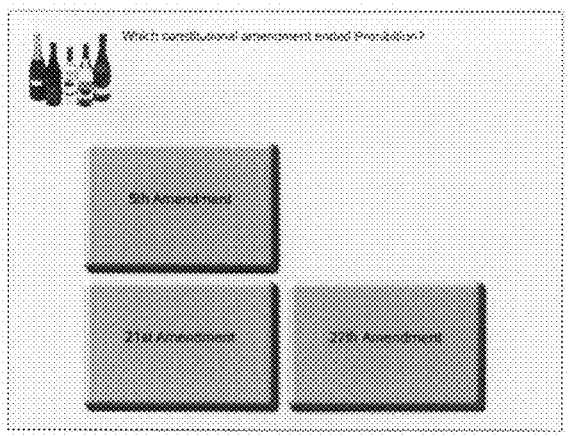

Choosing a wrong choice causes that choice to disappear. The Announcer will then say that it is the wrong choice, and encourage the user to try again, state the number of choices left, and repeat the question.

FIGURE 10I

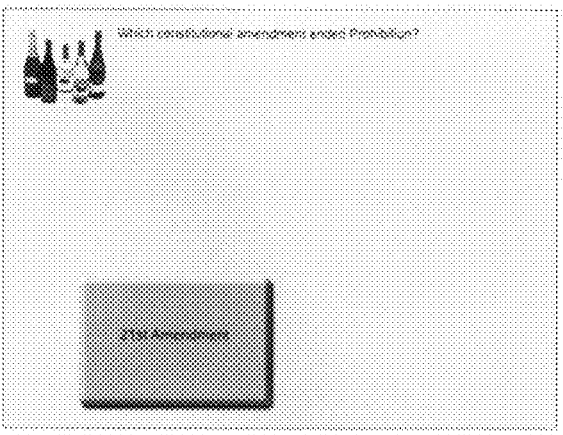

Choosing the correct answer makes all other choices disappear, and the Announcer congratulates the user.

FIGURE 10J

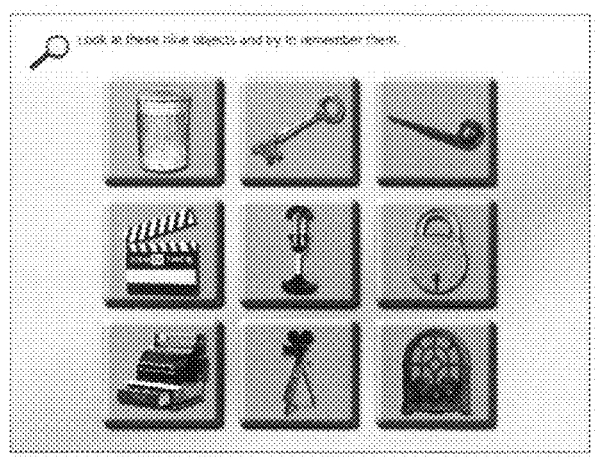

Another event that may occur may involve more than a question. In this case, the Announcer tells the user to take 10 seconds to look at these nine objects, and try to remember them.

FIGURE 10K

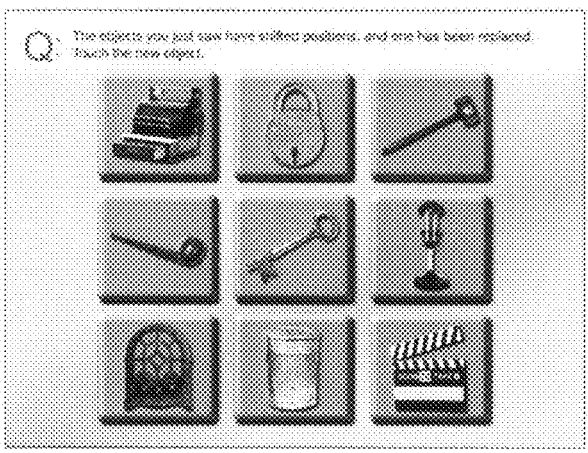

In this event, the Announcer says that the objects have shifted, one has been replaced, and asks the user to touch the new object, encourages the user when the user chooses the wrong answer and congratulates the user upon choosing the correct answer.

FIGURE 10L

This event is called "Keep Your Eyes Open!" where the user has to keep observant on the following scene to answer a series of questions.

FIGURE 10M

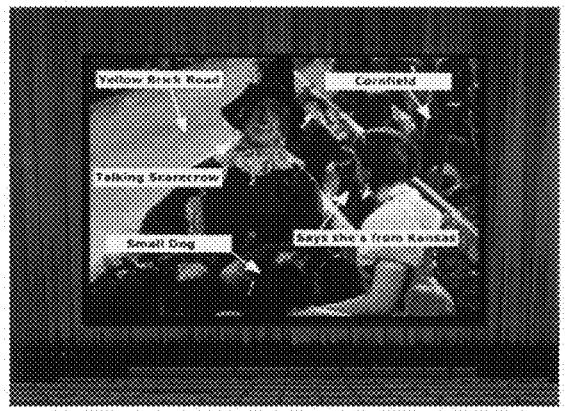

The event shows an example, in this case from the scene of "Wizard of Oz," and points out various objects that could be used in a question. All movies are shown in a theater setting.

FIGURE 10N

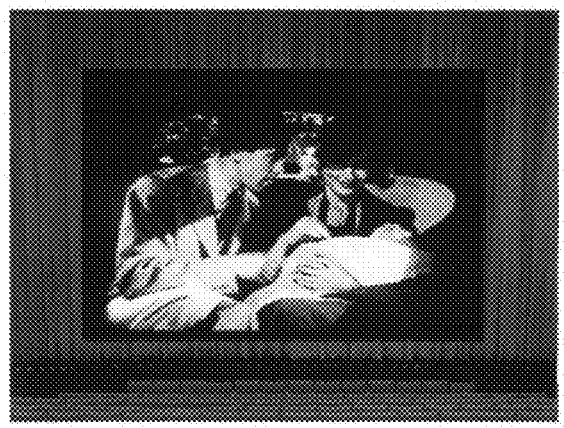

In this movie clip from the 1939 movie "Made for each Other", actors James Stewart and Carol Lombard ride in a taxi with their new baby, and, the system continues with questions from the scene.

FIGURE 10O

One question asks, "Where does this scene take place?" The user will have to remember that it is "In a Taxi."

Another question may ask what are the names of characters the actors were playing. Here the answer is Johnny and Jane.

The Announcer may ask the user to identify the actress who played the woman in this scene.

This event ends with the Announcer thanking the user for playing "Keep Your Eyes Open," and says, "see you next time!"

Another event that the system holds is called "Hidden Words."

This event involves the user being presented with a phrase, and then identifying the objects seen below in that phrase. In this case, the word "flute" is seen in the phrase.

The system then begins the event, by showing the phrase and the list of items below.

Here the answer is "gavel," which the system reveals upon reaching the correct answer.

The scene ends with showing the beginning title card.

This event involves listening to a song that's the theme for a popular radio character, and the user is asked to identify it.

In this case, the system shows a poster used during World War II, and asks the user to identify the name of the person seen in the poster.

METHOD AND SYSTEM FOR PROVIDING RULE BASED COGNITIVE STIMULATION TO A USER

CROSS REFERENCE TO RELATED APPLICATIONS

This present application is a divisional of U.S. patent application Ser. No. 11/607,781, now U.S. Pat. No. 8,083,675, filed Dec. 2, 2006 and which claims the benefit and the priority date from Provisional Application Ser. No. 60/748,326, entitled Method and Apparatus for Providing Cognitive Stimulation, filed Dec. 8, 2005, the contents of which are incorporated in its entirety by reference.

BACKGROUND OF THE INVENTION

For the majority of the population, cognitive abilities decline with increasing age, significantly reducing quality of life. Studies indicate ongoing cognitive stimulation can mitigate this decline. They also suggest that the degree of mitigation increases with increased frequency and duration of such stimulation.

Systems and methods have been developed to test and train cognitive abilities. However, these systems make use of simple, repetitive tasks as testing and training stimuli, such as comparing the speed of two moving circles presented on a computer screen as taught in U.S. Pat. No. 6,632,174 to Breznetz. Although such tasks may be used to evaluate and train specific low-level cognitive abilities, they lack the variability, ecological validity, and entertainment value necessary to encourage and maintain long-term use and interest and without long-term use, their real-world therapeutic value is limited. Thus, there is a continuing need for endeavors that not only train low-level cognitive abilities, but do so in a way that is entertaining and relates to the real world to encourage long-term use.

SUMMARY OF THE PRESENT INVENTION

Briefly stated, the present disclosure describes an interactive cognitive stimulation system and method, designed to engage individuals in fun and challenging cognitive activities and exercises that will improve their quality of life and, in the case of non-demented seniors, slow or possibly prevent the onset of dementia. To ensure a high level of user interest, and to maximize real world relation, it engages user's (the term user and patient may be used interchangeably) in complex and ever-changing interactive, cognitive exercises which draw on real-world skills and subject-matter, and which are matched to each user's specific cognitive abilities, background, and interests. To further encourage continued and future participation, the format in which the exercises are presented is fun, entertaining, and, most importantly, unlike a tedious and laborious test.

Before a user's first session, an administrator (typically in an assisted living or senior care facility) or family member fills out a short "User Data" questionnaire for that user usually using a web-enabled application. In a stand-alone home application, the user data is entered usually by way of a keyboard, either a computer keyboard or a virtual keyboard appearing on a computer monitor (touch screen). Answers to the questionnaire provide the basis of obtaining generally two types of information: demographic information and cognitive information, related exclusively to the user. An embodiment of the disclosure (system) uses the demographic information, including such items as date-of-birth, gender, language, culture, education, profession and likes and dislikes, to select appropriate content data from a stored data base, presenting the user only activities relevant to his/her background, interests and age. Cognitive information is then used to set the initial levels of challenge of exercises presented to the user in their first session.

Providing each user with a unique program tailored to his specific abilities, interests and experience requires the identification of the specific user prior to the start of each session. Facial recognition technology has been adapted to accomplish this goal. To begin a session, the user sits facing a touch screen, presses a notated button on the first screen to commence operation of an identification process. A button represents a notated or identified portion of the screen that the user contacts to identify his input, selection or response. This signals the built-in digital camera to take the user's picture. The system searches its database for a picture that matches the user's picture. In the most common scenario, when a match is found, the user is automatically logged in. In certain arrangements, where for example the system is dedicated solely to a single user, normally in a home environment, the mere act of turning the system on, satisfies the user identification process.

After confirming the user's identity, the user commences a session. During the session, the user participates in activities and exercises addressing six cognitive domains: long-term memory, short-term memory, calculation, language, visuospatial, and critical thinking, all interacting through the touch screen interface. When a user answers a question he/she receives immediate verbal, audio and video feedback, and voice encouragement.

If a user answers a question, puzzle or game "correctly," the user moves on to the next exercise. However, if an answer is "incorrect," the user receives encouraging verbal feedback and direction, which eventually results in the user being guided to the correct answer. In this context, it is very important to appreciate that the user never 'fails' or answers "incorrectly," but rather nevertheless, receives self esteem supporting positive reinforcement and encouragement.

If a user does not answer a question within a time representative of his/her normal response expectation, the user is prompted to "take a guess, if the user is unsure of the correct answer." If after two prompts, the user still doesn't respond, the user is directed to the next exercise after a conciliatory transition, such as for example, "This one is really tough. Let's try something else."

If a user consistently misses questions for a particular cognitive domain or takes an inordinately long time to answer questions, the sequence of inquiries is adjusted to give the user easier questions for that domain. This prevents feelings of failure and frustration that could lead users to quit, but instead, promotes a sense of success, building feelings of accomplishment, self-confidence and self-esteem. Similarly, if the user answers all questions for a particular cognitive domain correctly and at a fast pace, the inquiries are adjusted to give the user more difficult questions more appropriate to his/her mental capabilities in that domain. Users will often receive non-challenging and entertaining optional rewards in the form, for example, of a movie or music clip. Over time, the user in a care facility environment or those users connected to a central office via the internet may also receive more tangible rewards and acknowledgements of their accomplishments through the mail.

Throughout the session, the user's response patterns are recorded and are used to update the user's mental status settings by domain. The mental status data provides the basis for the system undertakes statistical analysis and send alerts regarding changes in patterns of user performance. A significant decline in a user's performance (e.g. speed and/or accuracy of response) could indicate a possible change in medical condition including a stroke or an adverse drug interaction. The system can be programmed, with the permission of the user, to send an alert via email to the user's caregivers, physicians and family members if it detects such declines.

DETAILED DESCRIPTION

Figure 1:
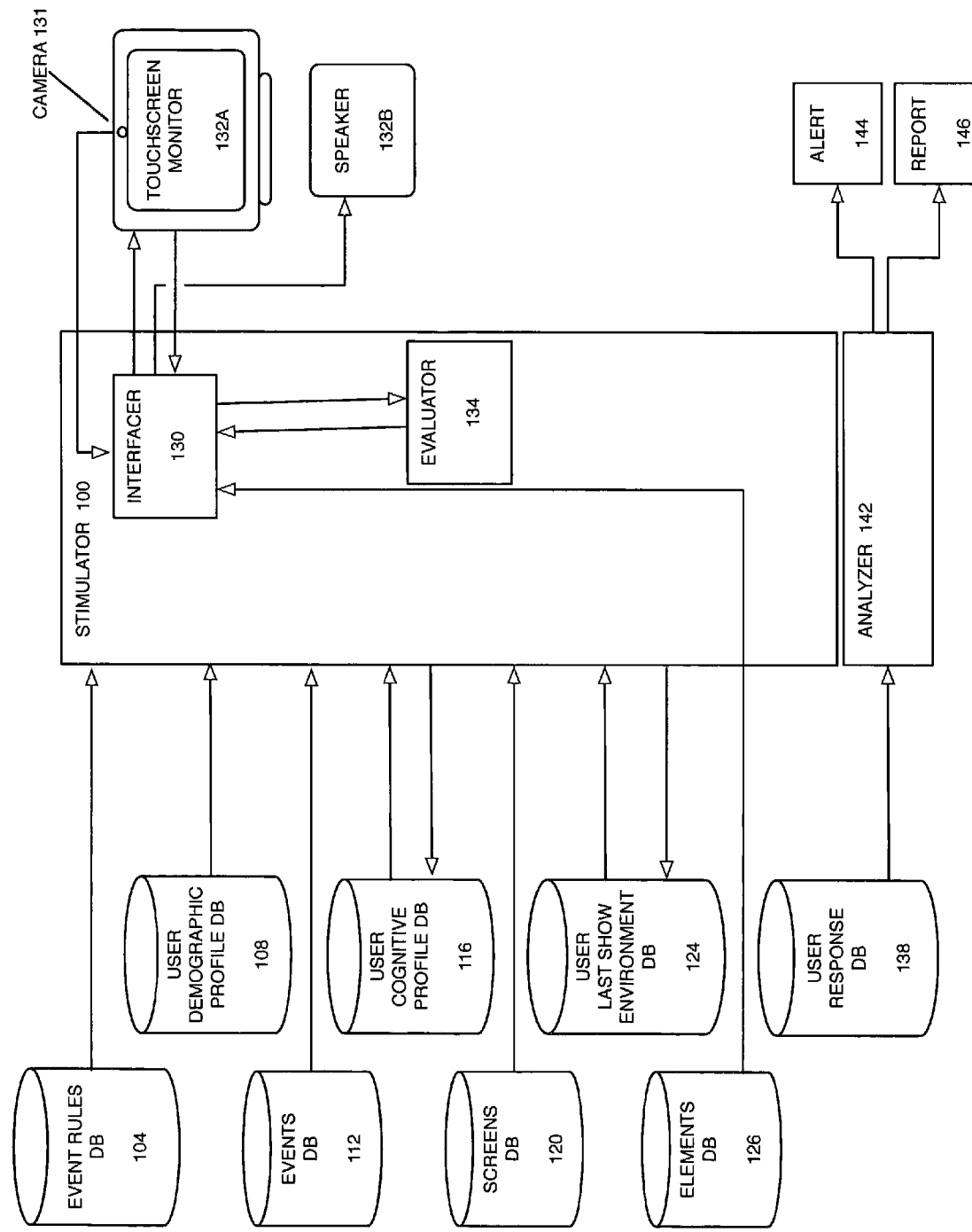
FIG. 1 is an illustration of a block diagram of the general components of a system to provide adaptive rule based cognitive stimulation to a user according to an example embodiment of the present invention.

FIG. 1 is an overall simplified block diagram of an example embodiment of the system of the present invention. Stimulator 100 is microprocessor based and is configured to process information, namely User Data for inclusion and update of a User Profile and Content data. In the present embodiment, the device uses information contained within various databases to interact with the user. The databases that are represented in FIG. 1 are: Events Rule Database (104), which contains the various rules used to decide when and how events are to be displayed to the user, further described below; User Demographic Profile database (108), which contains the information from the general profile of the user (such as native language, date of birth, likes and dislikes, etc.); Events database (112), which contains the list of information on each event (like Hidden Words in FIGS. 10T-10X, representing the entire event); User Cognitive Profile database (116) which has the user information relating to their cognitive levels and mental status (further described below); Event Screens database (120) which contains the individual screens in each event (example, each individual screen in Hidden Words shown in FIGS. 10T, 10U, 10V, and 10X); User Last Show Environment database (124), where information on the last various events the user has seen is stored; Event Screen Elements database (126), which contains the various elements of an event screen (example, button graphics, video clips, pictures, etc); and User Response Database (138), where all the responses to the events shown the user are stored. The Stimulator 100 includes a number of operations that perform functions necessary to interact with users, namely: an Interfacer (130), and an Evaluator (134). Depending on the event screen selected (based on rules described below), the Interfacer (130) retrieves all the relevant visual and audio cues that comprise that event screen, such as button graphics, movie clips, pictures, etc.

The system provides the described information from the Event Screen Elements database 126, and presents it to the user through the touch screen monitor (132A) and/or Speakers (132B). The user then responds by means of touch screen monitor (132A) monitor, and those responses go back through the stimulator 100, to the Interfacer (130), and then to the evaluator (134). The evaluator (134) processes the user responses, and provides the processed responses to the User Response database (138). The evaluator (134), from the user's response, determines whether the user is ready for a "more difficult" event, or should receive an "easier" event or maintain the same level of event difficulty in continuing with the presentations. The evaluator (134) is also responsible for providing the audio cues to the user depending on the user's response, such as "that's right!" or "try again!" The stimulator 100 also provides user response information to the User Cognitive Profile database (116) and the User Last Show Environment database (124). During use, these databases that receive information from the stimulator 100 will build upon and update the user profile as well as add additional information that the device uses in future interactions with that user.

Figure 3:
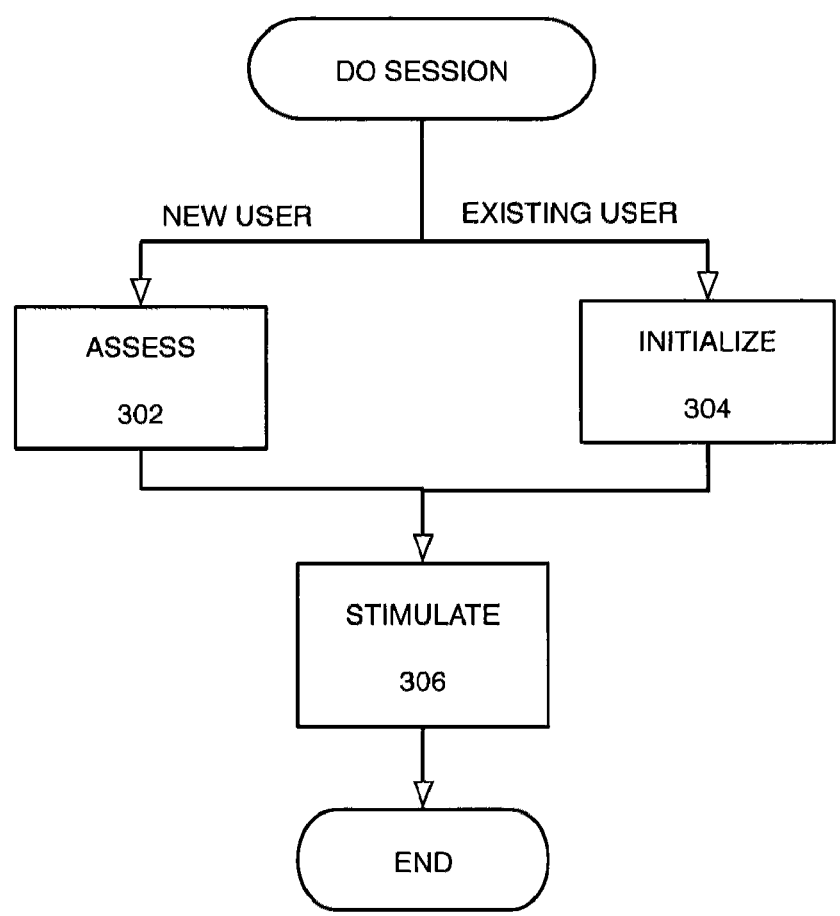
FIG. 3 is a flow chart to determine initial system tasks based upon the nature of the user, in accordance with an embodiment of the present invention.

The User Response Database provides information it has received to an operation called the Analyzer (142), which analyzes the user's response. While operations undertaken in the Evaluator (134) occurs in real-time, the Analyzer (142) typically processes information during nonuse intervals or during user sleep time. The Analyzer undertakes checking the user's responses for any possible signs indicative of problems regarding the user's health. Depending upon the results of the analysis, the Analyzer (142) will either communicate to the user with an Alert (144) which provides emergency information to caregivers, physicians and/or family members, or communicates with a Report (146) to caregivers, physicians and/or family members The Stimulator 100 initiates a session as shown in FIG. 3 at step 300. As will be described in more detail later regarding FIGS. 10A-10E, the system using stored photos and facial recognition technology, attempts to identify the user. In doing so the system determines, by way of the user profile data, whether to commence further operations depending upon whether a new user or existing user is participating in the session. In the event a new user is detected then an assessment at step 302 commences. The assessment retrieves first the user's demographic information, then the user's cognitive information from the questionnaire. If an existing user is detected then an initialize function is undertaken at step 304. Initialization first retrieves the user's demographic information from the questionnaire, then retrieves the user's cognitive information from the User Cognitive Profile Database 108 continually revised during previous user's sessions. Upon completion of either assessment at 302 or initialize at step 304 a stimulate function at 306 is undertaken.

An embodiment of the present invention utilizes two different kinds of data: User Data and Content Data. Initially, the user will provide "User Data" that is basically the user profile, representing information about the user that can affect how the system interacts with the user, and creates a user profile that is constantly being updated through continual user interaction. In a preferred embodiment, the user profile information is gathered via an Internet link (a remote application). It is a compilation and representation of the users' recorded experience over several months and even years using the system and method described herein. The initial user "baseline" information includes demographic information about the user, which is filled in by a questionnaire answered either by the user or a caregiver, which may include, for example, but is not limited to name, date of birth, country of origin, language (first language/other language spoken/language preferred), residence history, hobbies, vocation history, special interest areas, family member's names and their relationship to the user, vision limitations, and hearing limitations. User data also includes the cognitive functional level of the user, which details the cognitive ability, or Metal Status (MS) of the user, described as Stage 1 (L1—normal high functioning), Stage 2 (L2—normal), Stage 3 (L3—normal brain aging), Stage 4 (L4—mild cognitive impairment), and Stage 5 (L5—mild to moderate dementia). Any references to a user's "stage," will mean the level of their cognitive ability.

Content Data

Figure 2:
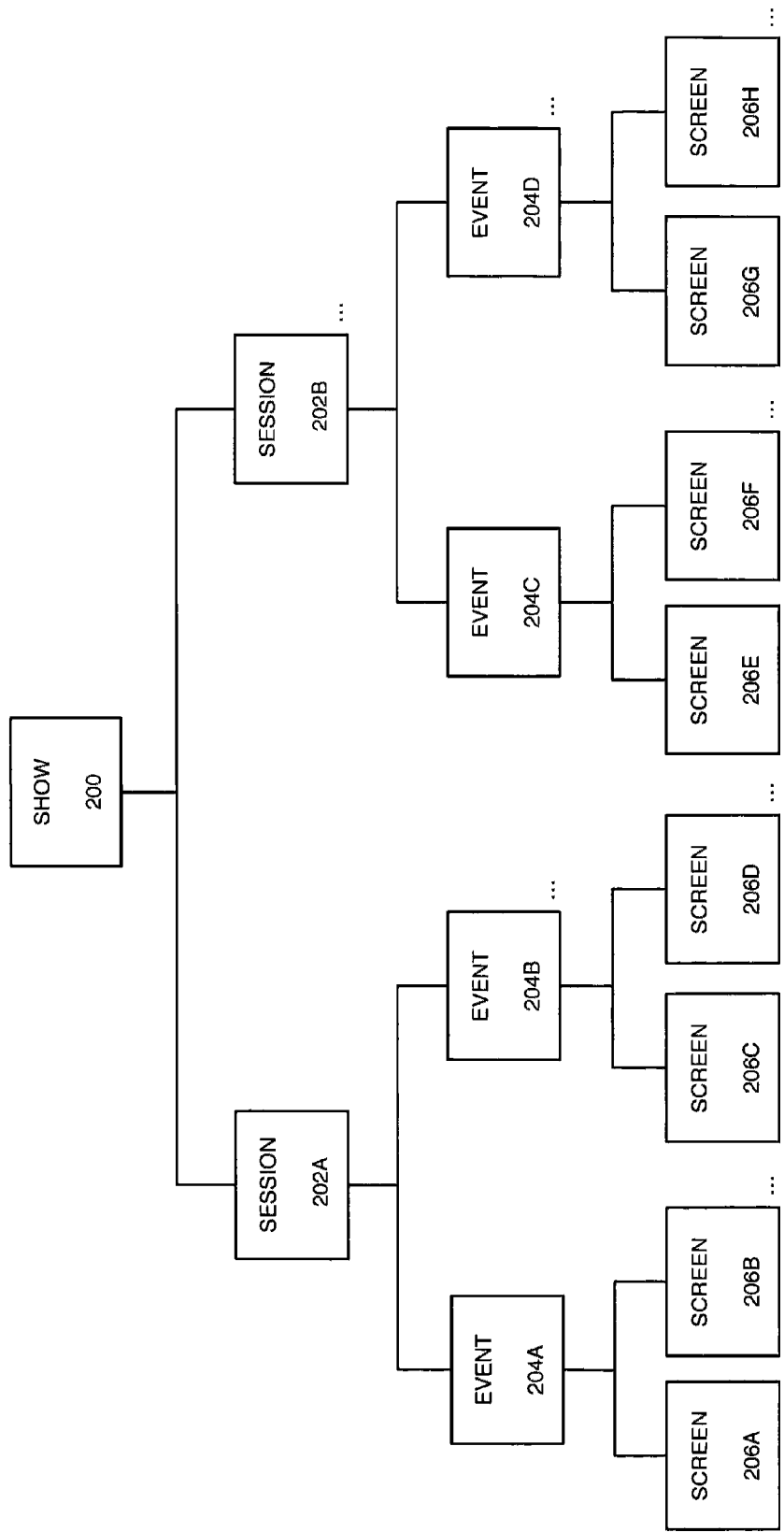
FIG. 2 is an illustration of a hierarchy of components of a show which includes sessions, events and screens in accordance with an embodiment of the present invention.

Content data, which is independent of user's recorded experience, may take the form of general information inquiries, recognition and problem solving exercises, such as for example, completing puzzles and the rewards may take the form of audio-visual recognition aimed at providing re-enforcing and motivational encouragement to the user. FIG. 2 is a representation showing the hierarchical structure of the content data and its subparts. A show 200 represents the entire user's experience which can last over several months or years. This show 200 may consist of any number of session 202$s$ (i.e. 202A, 202B, etc.), one or more per day. A session 202 represents user experience with the system in one sitting, which may last minutes to hours. For example, referring to FIG. 10, the entire Figure is considered one session. A session 202 may consist of any number of event 204$s$ (i.e. 204A, 204B, 204C, 204D, etc.), which represents the smallest "unit" of a user's experience of the device during a session. Event 204 may consist of a single stimulus-response interaction (typically one screen) or multiple stimulus-response interactions (multiple screens). This can include a presentation of a "reward" (movie and music clips, trivia, fun facts, photos) in response to a "correct" user answer.

There are a variety of event 204 types, which include but not being limited to: a demographic questionnaire, Login (user authentication), Main Title (an A/V presentation that displays every session, typically just after the login event), Volume-Adj (a series of screens to allow the user to adjust the volume of the speakers or headphones to their preferred level), Orientation (a quick audio/visual review of how to use the system), Review (an A/V of high points from the users last session 202), News (an Event presenting something involving current news), Question (an Event presented in question format, requiring a single response), Story (an event presented in story format, which may involve multiple user stimulus/response interactions), Puzzle (an event that acts like a well-known puzzle format, like Tic-Tac-Toe), PhysEd (an Event designed to lead the user through physical exercises), Motivation (an A/V presentation designed to improve the users outlook or motivate the user), Entertainment (an A/V presentation just for fun).

Again referring ahead to FIG. 10, an event would consist of the presentations illustrated in panels 10H-10J, 10K-10L, 10M-10S, 10T-10×, and 10Y-10Z. An Event 204 may consist of one or more event screen 206$s$ (i.e. 206A, 206B, 206C, etc.). These event screens are what the user actually sees and interacts with. An event screen may consist of various event screen elements such as audio from System Speakers (132B) (i.e. music, sound effects), graphic (i.e. images, illustrations, line art), and/or video from touch screen 132A (i.e. movie clips, animations) that also interacts with the user and aids with the user stimulation process. These are illustrated in FIG. 10, with the graphic, photos, and movie clips seen in each individual panel.

The system can be set up to function in a user's home, medical facility, senior care community, community center, therapeutic center, senior day care center and any similar area. The preferable set up of the system is for the user to be positioned facing the touch screen 132A, so that the Camera (131) can focus on their face. The Camera 131 preferably positioned at the top of the screen will scan the user's face, and use facial recognition technology to identify the user based on a previously scanned photograph normally obtained at initial user data entry. The system proceeds to identify the user and load the appropriate data, such as the user profile and prior use history. After confirming user identity and loading the appropriate data, the system commences a session. The system will either Initialize (if the user has used the system before) or Assess (if the user is using the system for the first time). Subsequently, the system will proceed to user stimulation (further discussed below).

Throughout this session, the stimulation process will include multitudes of various events types which include but are not limited to: DemoQ (demographic questionnaire), Login (user authentication), Main Title (an A/V presentation that displays every session, typically just after the login event), Volume-Adj (a series of screens to allow the user to adjust the volume of the speakers or headphones to their preferred level), Orientation (a quick A/V review of how to use the invention), Review (an NV of high points from the users last Session 202), News (an event presenting something involving current news), Question (an event presented in question format, requiring a single response), Story (an event presented in story format, which may involve multiple user stimulus/response interactions), Puzzle (an event that acts like a well-known puzzle format, like Tic-Tac-Toe), Phys Ed (an event designed to lead the user through physical exercises), Motivation (an A/V presentation designed to improve the users outlook or motivate the user), Entertainment (an A/V presentation just for fun).

There are a variety of sources of stimulation the system selectively uses that include a variety of events (based on, but not limited to fine art, historical events, pop culture, inspirational messages, exercise activities, meditation activities, and spiritual activities). The sessions may include certain special events, such as an ending event or events including a teaser/preview/cliffhanger for motivation for the user to return, and a starting event or events involving the promised activity/exercise from the teaser/preview. The system may present user personal items such as addressing the user by their name, acknowledging their birthday, and/or an inclusion of events that have user specific photos, sound bites, home movies/videos of user/family activities that include family and friends or with places and/or events user is personally familiar with, and questions relating to stored user data (as an example, "how old were you in 1952?). There may be questions that could: be in a multiple choice form; involve events that include movie and music clips, sound effects; involve "radio theater" style vignettes; include "rewards" for getting "correct answers, that include movie and music clips, trivia, fun facts, photos; and involve character voices to help illustrate concepts. There also may be a voice over announcer or host to: present the stimulus to the user simultaneously with the on screen (written in type) stimulus; provide positive, directional, or correctional responses to user input; provide what appears to be randomized feedback responses to users using a "round robin process,"; prompt users to take a guess if there is a pause or interval without a response; and provide time orientation.

The system described herein, provides other types of auditory feedback, such as escalating "dings" for "correct" responses. Cognitive domains exercised by such stimulation includes but are not limited to Short Term Memory/Delayed Recall, Long Term Memory, Language, Visual (includes visuospatial and visuoperceptive), Critical Thinking (includes Concept formation, sorting, patterns, logic/reasoning, planning, flexibility), and Mathematical. In an institutional setting, an administrator may choose session duration (typically 30-45-minutes, based on scheduling requirements). An embodiment of the invention will adjust the session (events 204) to match the chosen duration independently of the application of the rules, which determine Event sequence. This shall give the user a sense that there is a beginning (a ramp up, easier events to start), middle (a break, particular events), and end to each session. The user will then feel as if he/she has "completed" a session, rather than experiencing an abrupt interruption or a forced ending.

After completion of a session, the system stores all the data it has attained to analyze for future interactions with the user. The system provides reports and any important alerts regarding the user's performance to caregivers, physicians and family members involved with the user's well being. In the event that a user is in communication with an institutional system installation by means of an internet connection, the user system and the home base server can exchange information, which allows the home base server to analyze the user data, upload new content, upgrade software, and diagnose any possible problems with the device. While the system can operate standalone, the default function of the system is to cease operation if the system has not communicated with the home base server for longer than two (2) days. For environments such as retirement and senior care communities where multiple systems are in operation, an alternative manner of downloading content or other similar types of communication with the home base server may ensue. Among the devices in that location that are connected to their facilities' network, the devices will choose one of them to be the "master," which can change each time such a communication is made. This "master," will be the first to download the content, and then through the facilities' network spread that download or similar communication to the rest of the systems. Upon starting a new session, as mentioned above, the device will remember past interactions with the user, and continue to build upon the user's profile to better conform to the user's needs and ensure maximum stimulation.

Software

FIG. 3 illustrates a very basic overview of a Session 202. First at step 300, a session begins. If this is the first session for the user, then the system will continue with step 302 Assessment, depicted in detail in FIG. 4 described below. If this is not the first session the user had experienced with the system, then the system will instead start step 304 Initialize, depicted in detail in FIG. 5 also described below. After the assessment or initialization, the device will continue with step 306 Stimulate, further described below.

Figure 4:
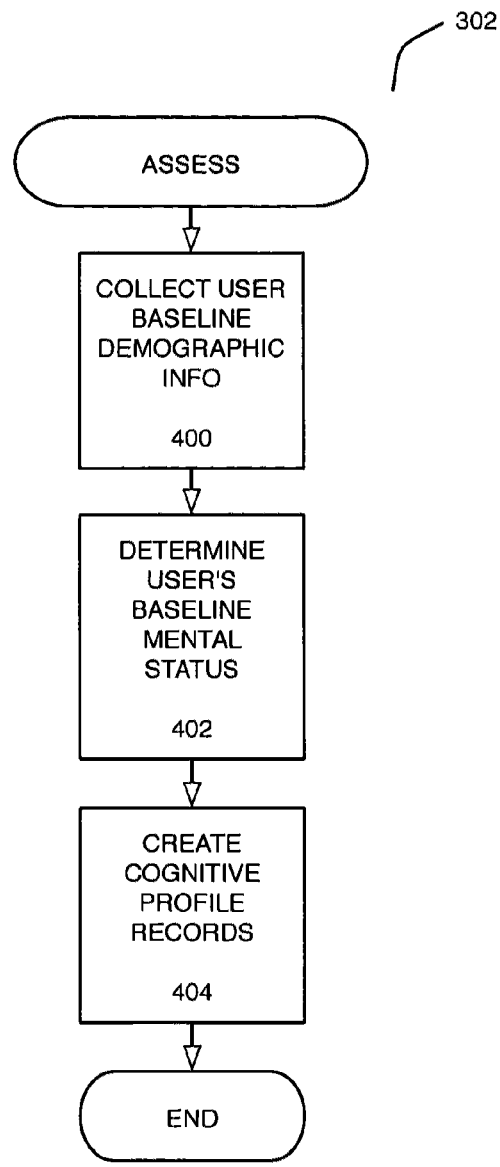
FIG. 4 is a flow chart illustrating the creation of cognitive profiles of the user, in accordance with an embodiment of the present invention.

FIG. 4 illustrates the steps taken in an Assessment (step 302), the operation that occurs when a new user starts a new show. At first step 400 the system collects the user's baseline demographic information from the User Demographic Database 108. The system at step 402 determines the user's baseline mental status. In determining the user's baseline mental status, Stimulator 100 performs a process identical to step 400, but does so using events from the event database 112. After the user's baseline mental status is determined, the system at step 404 creates a cognitive profile record. It also records the same mental status determined in step 402, in a User Cognitive Profile database 116. The device uses the single baseline in all the user's cognitive profile records as a starting point for selecting events from the Event Database 112 of appropriate difficulty to present to the user during each Session. After the starting point is determined, the system will proceed with stimulating the user.

Figure 5:
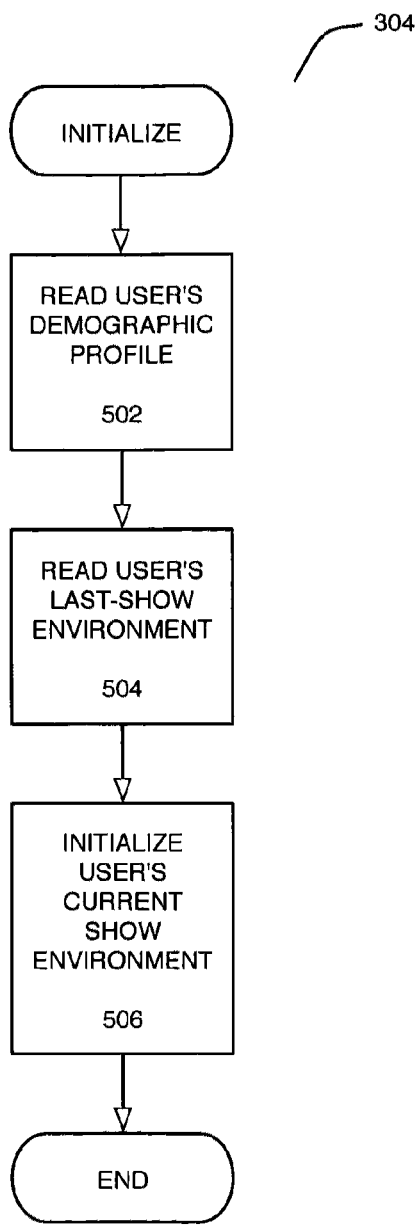
FIG. 5 is a flow chart illustrating the initialization of a user's current show environment, in accordance with an embodiment of the present invention.

FIG. 5 illustrates the steps taken in an Initialization procedure 304, the operation that occurs when a user who has used the device before, starts a new session. This operation retrieves from databases 108, 116, 124 and 138 all information necessary to conduct a current session 202 in a manner informed by user data stored by stimulator 100 in previous sessions 202s. At step 500 the system reads the show rules pertinent to the show to be presented. The show rules are organized to properly conduct a presentation through the events and screens to be utilized.

At step 502, the system reads the user's demographic profile from the User Demographic Profile database 108. At step 504 the system reads the user's Last-Show environment, by retrieving the user's information from the User's Last-Show Environment Database 124, as well as counters (further explained in the Next Rule to Apply section below) reflecting the number of Events 204 that have occurred since the last presentation of Events in each of the cognitive domains. This exercise ensures that repetitive and in some cases, non-suitable events, due to either ease or difficulty or complexity, are not presented in a current show. Accordingly, both the challenge level and interest level to the user is maintained at a value proper for the current user. At step 506, the system initializes the user's current show environment and proceeds with stimulating the user.

For processing the large number of possible events to provide cognitive stimulation for the user, an embodiment of the system has a set of "event rules." The event rules determine both the sequence and manner in which way the Sessions and Events are presented to each user. Instead of "pre-programming" the Sessions and Events (which may give a sense of repetitiveness and not properly address the users interests, needs, nor provide needed day-to-day variations in cognitive ability), the system uses an "adaptive response" technique embodying a concept named, "the next rule to apply" which is discussed further below. A novel aspect of an embodiment of the present invention is that the adaptive response technique makes each session unique for each user, every time it is used.

Figure 6:
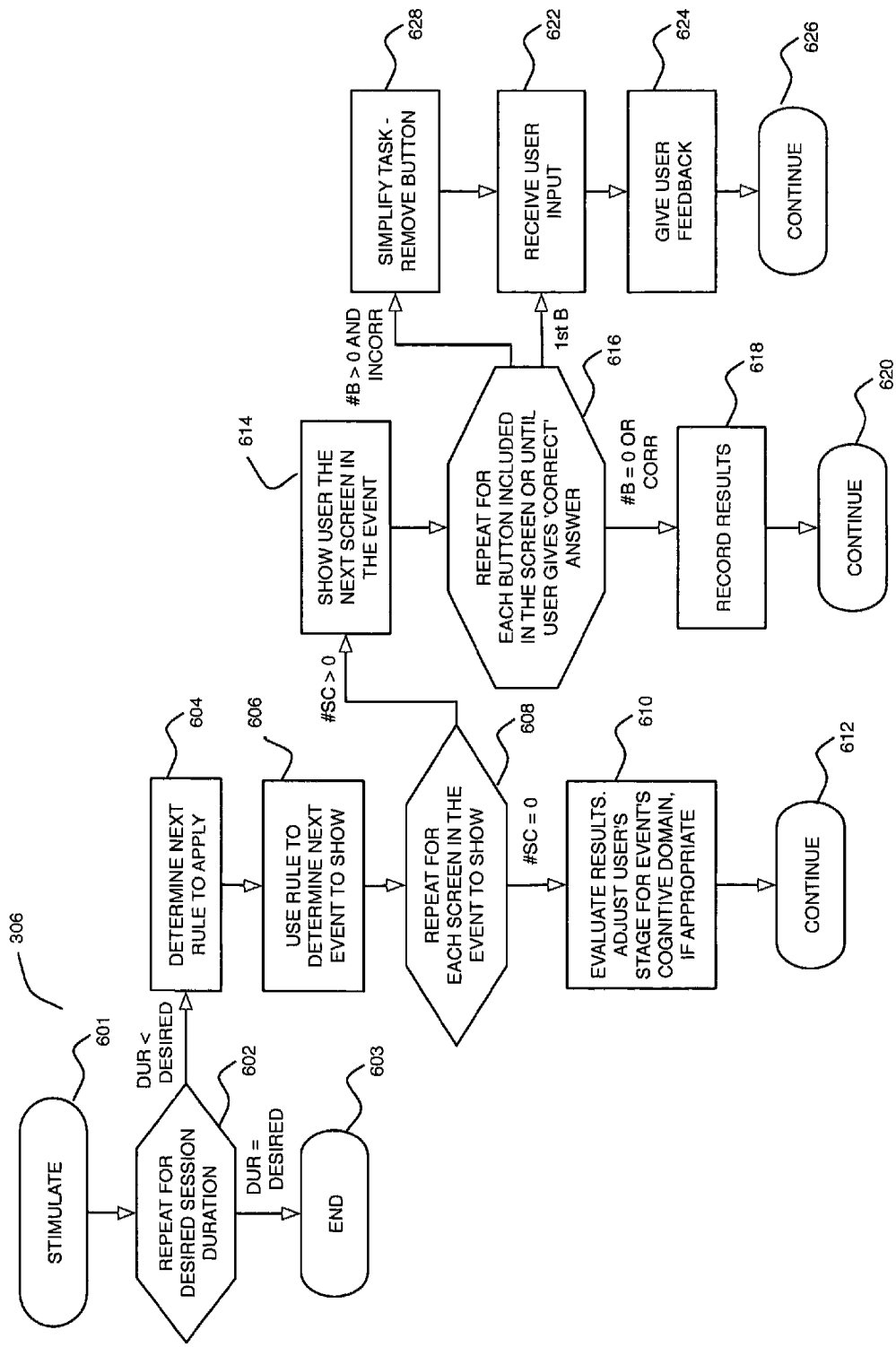
FIG. 6 is a flow chart illustrating the sequence of event occurrences and interaction with a user, in accordance with an embodiment of the present invention.

The steps involved in determining the sequence of event occurrence and interaction with the user is shown in FIG. 6. Upon the start of the cognitive stimulation process at step 601, the stimulation may continue for the length of the predetermined duration (DUR) of the session at step 602. After the desired session duration is reached, cognitive stimulation ends at step 603. If the current duration time is less than the desired duration time, the system determines the next rule to apply at step 604. Next, the system uses the determined rule from the previous step to determine the next event to show (606). Each event has a certain number of event screens, and so that event comes with a starting event count above 0, and as the event progresses the number starts to count down as each event screen is presented. After determining the rule to be used, the system presents the screens to the user until the Event Screen Count (SC) reaches zero at step 608 which is reached after the system presents the final screen 206 of the event 204 (see FIG. 2). Each different event has an associated screen count which represents the number of different screens contained within the particular event. The screen count number depends upon and varies as a function of the type, complexity and objective of the event currently being presented.

The system then evaluates the user's responses and, if appropriate, changes the value stored in the User Cognitive Profile database 108 for the current user and the current event 204's primary cognitive domain (part of the self adjustment function) in step 610. If the screen counts are above zero, the device will continue to show the user the next screen in the event in step 614. These screens will display a screen 206 of event 204, which includes giving a query and displaying buttons for the user to contact to receive the user's response. Depending on the type of screen and event, the screen will continue to be shown to the user until the button number (B) equals 0, or the "correct" button has been pressed in step 616. After the button number (B) reaches 0, or the "correct" button has been chosen, the system then stores the response time and the number of attempts necessary to get a "correct" response for each Screen 206 of the current event 204 in step 618. In the instance that the number of buttons is greater than 0, or is the "incorrect," button, the system decreases the complexity of the stimulus at 618 in each stimulus-response possibility on each screen 206 from which the user can choose, or provide a verbal or visual hint, or both at step 622. The device receives the user's input at step 620, for each stimulus-response possibility on each screen 206 of event 204, and then gives the user encouraging feedback after each response at step 622 based on his or her response and the results are recorded at step 624.

Rules and Events

A salient feature of an embodiment of the present system is its rule-based procedure for determining what content the user is presented, and the time of presentation. The rule-based procedure by which an embodiment of the present invention chooses content for a user relies upon rules regarding the characteristics of the content to be shown to users, rather than identifying the exact content to be seen by each user. In addition, the procedure ensures that users will not see content inapplicable to them, and allows session times to be of any length, since the content at specific percentages of the session time may be specified.

The rules are an important tool for controlling each user's experience during a session using the system described herein. The two main aspects of this experience are show contour and show variability. The show contour provides a continuum of presentations through a session in order to provide the user with the feeling that they are smoothly proceeding from the beginning stage, through the middle stage to ending stage of a session, rather than just experience an abrupt start or an abrupt end with the potential of causing some uneasiness and anxiety in the user. Show variability refers to making the show seem new and novel at all times in order to avoid giving the user a sense of repetitiveness in event or show presentations. It is important to control the show contour because, as in a television episode, each user session is a self-contained episode and must have a beginning, middle, and end. Sessions of any length will contain all these elements of the show contour. Additionally, it is important that the show be unpredictable because, without variability, users are likely to become bored and stop using the system and thereby discontinue the cognitive stimulation benefit provided by using the system.

The table below illustrates an example of rule protocol in a user session:

| Rule # | Cognitive Domain | Level of Functioning | Minimum Frequency | Sequence Number |
|--------|------------------|----------------------|-------------------|-----------------|
| 1 | Long term memory | Normal High (L1) | One per 5 events | 1 |
| 2 | Long term memory | Mild Cognitive Impairment (L4) | One per 5 events | 2 |
| 3 | Short term memory | Normal High (L1) | One per 7 events | 3 |
| 4 | Short term memory | Mild Cognitive Impairment (L4) | One per 7 events | 4 |

The rules are chosen based on the user's cognitive profile and last show environment. In this example, if the user is high-functioning (L1), then either rule 1 or 3 will apply. The system then attempts to choose a rule based on the minimum frequency specified. If the user has not seen a long-term memory event in the last 6 events, and has not seen a short-term memory event in the last 8 events, then again, both rules 1 and 3 qualify because the user has not met the minimum frequency requirements for both rules. In this case, the sequence number determines which rule is used next. Since rule 1 has a lower sequence number than rule 3, rule 1 is the rule chosen.

Once rule 1 is selected, it will guide the system in choosing the next event to show the user. Rule 1 requires the system to look in the events database for an event that exercises the cognitive domain of long term memory. The event must also be at a high difficulty level, since the rule chosen indicates that the user's level of functioning is high. Finally, the event must match the user's demographics, as collected in the initial questionnaire. In a similar fashion, if the user level of functioning is mild cognitive impairment (L4), then either rule 2 or 4 will apply and since rule 2 has a lower sequence number than rule 4, rule 2 is chosen. The selection of an event according to rule 2 then follows with the above considerations, relating however, to mild cognitive impairment rather normal high.

To explain the way in which the rules accomplish their purposes, it is important to discuss the organization of the content seen by the user. A show consists of self-contained building blocks called events, which may be of varying lengths and complexity; they are strung together, bead-like, according to the Rules. Events are organized in a hierarchy that includes Domains, event types, and event subtypes. Domains are the cognitive domains familiar to neuropsychologists, such as Long-Term Memory, Short-Term Memory, Language, Visuospatial skills, and two sub-domains of Executive function, Critical thinking and Calculation. There are also specific domains that serve to organize the content not corresponding to familiar cognitive domains. These unique domains include such categories that may be designated as "Spirit and Soul" and "The Center," a group of exercises that serve to relax and focus the user.

Each domain has several associated event types, which are higher-level groupings of events within the domain. For example, the Short-Term Memory domain has an event type called "Lists." Each event type, in turn, has several associated event subtypes, lower-level groupings of events within the event type. For example, in an event type identified as a "List", there is an event subtype called "Word Lists." Each event subtype is associated with one event type, and each event type is associated with one domain. With regard to the example above, the list identifies the category of the event type, and "word" as distinct from numbers as symbols, for example, defines the nature of the content of the "List". Another possible example of an event subtype, is "Tom's Grocery List."

Events are further categorized by Special Interest Area (SIA). When the users start their first session, they choose from a list of SIA's and indicate which ones they especially like or dislike. The rules ensure that the users do not see events in SIA's they do not like, and see a higher percentage of events in SIA's they do like. SIA's may include history, music, sports and pop culture as mere examples.

The two main purposes of the Rules, however, as discussed above, are to control the contour of the show and provide variation. As mentioned previously, providing show "contour" provides the user with a sense of a "beginning," a "middle," and an "end," so the user doesn't feel that his show had abruptly started and ended. Providing variation is also important to ensure that the user doesn't get bored with constant repeated events, and encourages repeated use. There are two rule types necessary to accomplish these two purposes. The first rule type is the Temporal Rule type; temporal rules specify which types of events will be seen at different time periods in each session. All the rules, including the temporal rules, tend to customize the presentation to the current user. The events identified by the temporal rules serve to orient the user at the beginning of each session and to end the session on a positive note. The second rule type is the Frequency Rule type; frequency rules specify how often a user will see a given type of event. Because these frequency rules control the minimum and maximum frequencies of event types, users will see a large range of different event types in a varied fashion.

It is desirable to further control the show contour by following difficult events with easier ones, or by following long events with shorter ones. This enforces variability in difficulty and rewards users for completing long or difficult events. To accomplish this, a third type of rule is necessary, defined as the post event subtype (PEST) rules. PEST rules specify event subtypes to follow other event subtypes. In most cases, the leading event subtype is a challenging, highly cognitively stimulating event, and the post event subtype is a rewarding event that involves reminiscence of music or film clips.

Each rule and event has various values associated with them. Some have "count" values (which can be defined in varying ways such as being the minimum amount of events needed before being implemented), or identifying "serial numbers," (an internal indicia identifying a specific user or event) or similar distinguishing indicia. Depending on the situation, these values are used by the system in different ways to either sort by their values, or make a choice among several choices depending on their counts.

Figure 7:
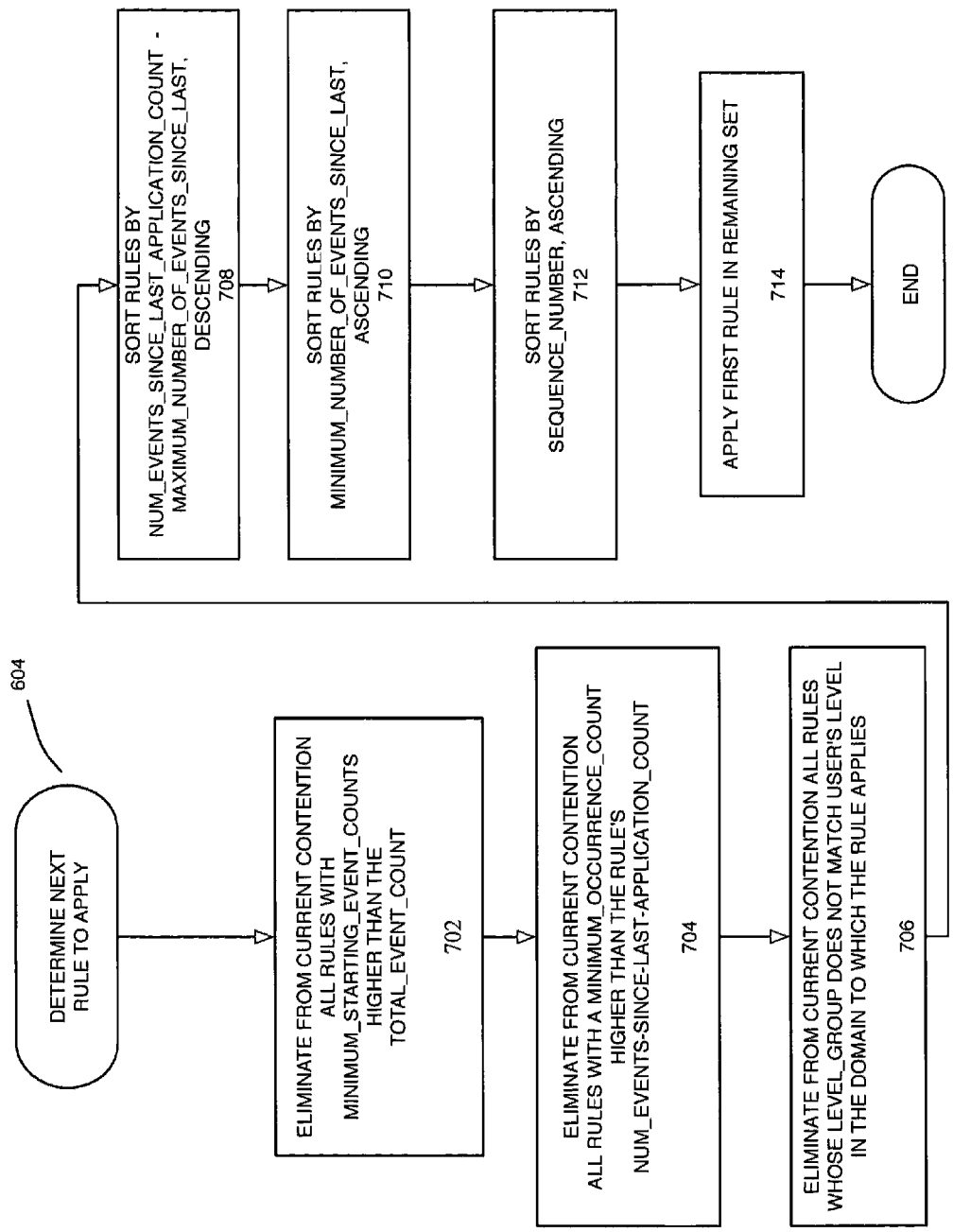
FIG. 7 is a flow chart illustrating the determination of the next rule to apply, in accordance with an embodiment of the present invention.

Determining the Next Rule to Apply (Step 604, FIG. 7)

Figure 10P:
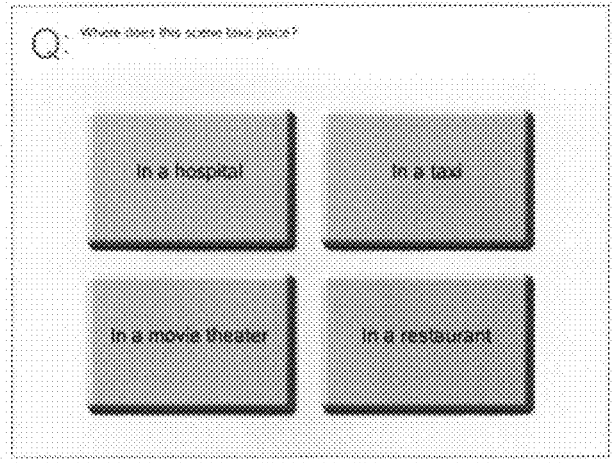
FIGS. 10a to 10z is an illustration of an example session including a sequence of events, queries, and system feed back to the user, in accordance with an embodiment of the present invention.
Figure 10Q:
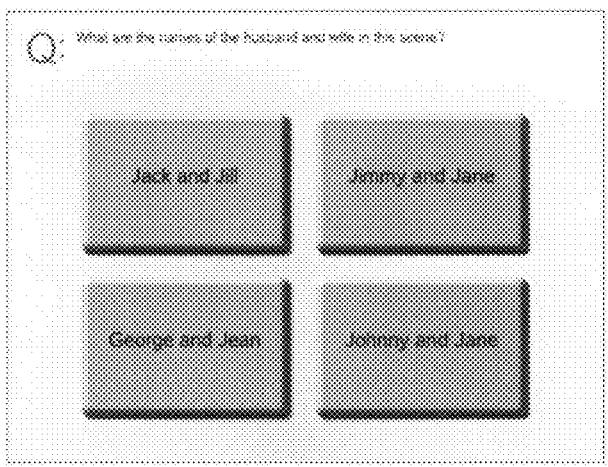
Figure 10R:
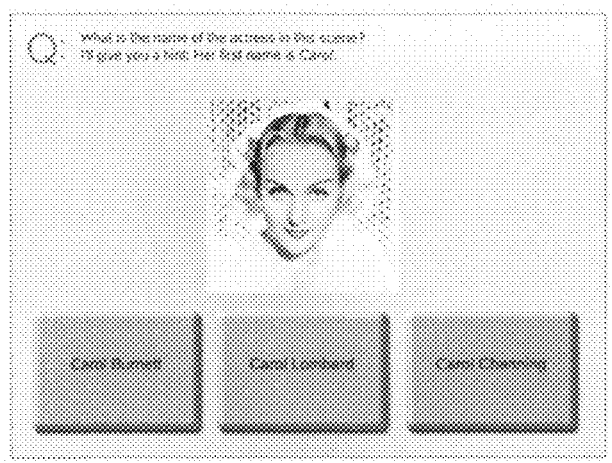
Figure 10S:
Figure 10T:
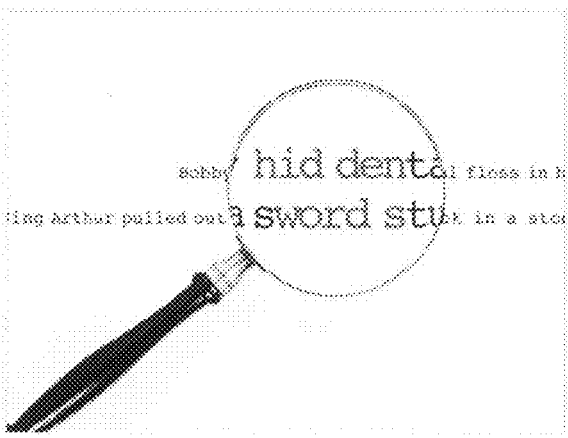
Figure 10U:
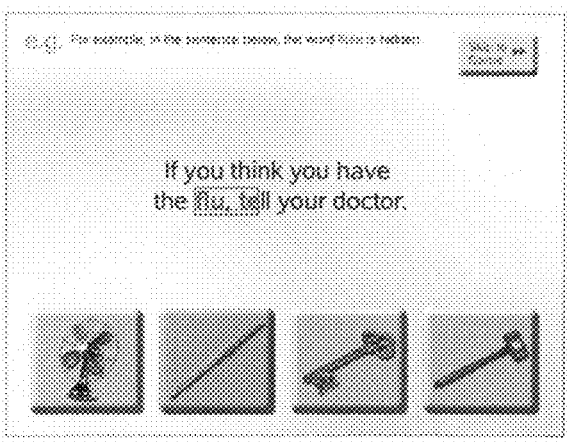
Figure 10V:
Figure 10W:
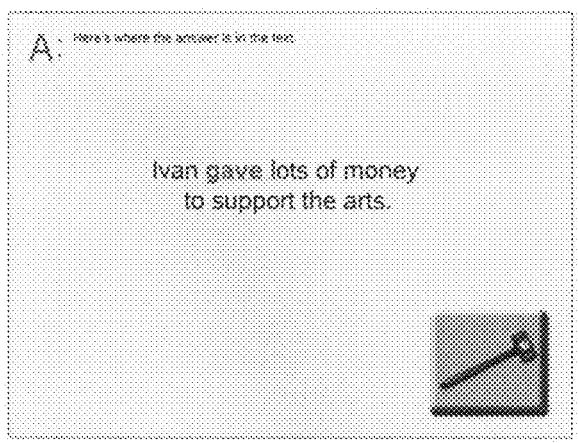
Figure 10X:
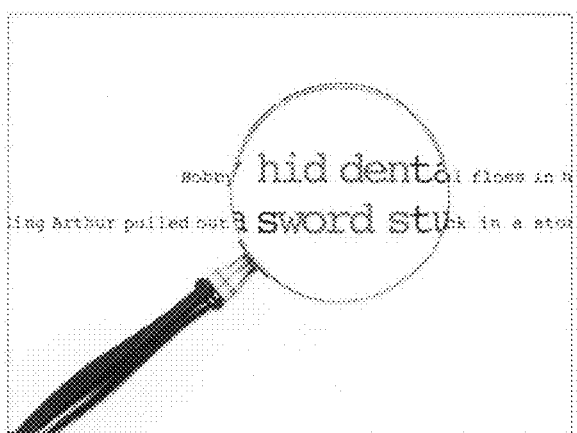
Figure 10Y:
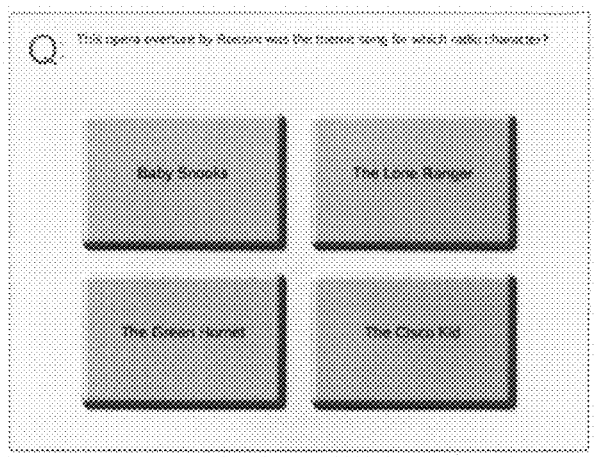
Figure 10Z:
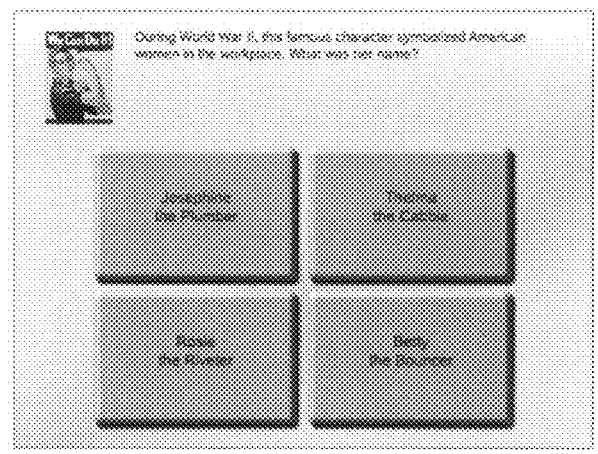

To further explain the procedure of determining the Next Rule to Apply, references is made to FIG. 7 which outlines the steps taken in step 604, "Determine Next Rule to Apply." With further reference to FIG. 10, determining the next rule to apply would take place before each event, that is, between FIG. 10G and FIG. 10H, and between FIG. 10J and FIG. 10K, and between FIG. 10L and FIG. 10M, and between FIG. 10S and FIG. 10T, and between FIG. 10X and FIG. 10Y, and between FIG. 10Y and FIG. 10Z, for example. As described above, each rule associated with certain events has a "Minimum-Starting-Event-Count" value. The "Minimum-Starting-Event-Count" means that the rule will not be applied if the total number of event's the user has been presented is less than the event count value that the rule has been given. Additionally, as the user continually uses the system, the system counts the number of events they've experienced and totals it into a "Total-Event-Count." The "Total-Event-Count," is the number of events the user has seen throughout an entire show.

In block 702, the system reads the "Total-Event-Count", and eliminates from current contention all other rules with Minimum-Starting-Event-Counts that are higher than that "Total-Event-Count." These higher-numbered events may not yet be appropriate for the user to experience, so eliminates those as choices of events to show the user. In the same fashion as the previous step, the system then eliminates from the current contention all rules with a Number-of-Events-Since-Last-Rule-Application-Count less than the Rule's Minimum-Occurrence-Count in block 704, resulting in providing significant variability. Next in block 706 the system goes through a final elimination process, by eliminating from current contention all rules whose group level doesn't match the user's level in the domain to which the rule applies.

The system then proceeds through a rule sorting phase, sorting the remaining rules by (number of events since the last application count)—(the rule's maximum number of events since last) in block 708, in descending order. The rule's number of events since the last application count indicates the number of events that have occurred since the last time that event category has been used, and the rule's maximum number of events since last value indicates the number of events that should occur between two events that are of the same subtype. Then a sort of rules by their "minimum number of events since last" in ascending order in block 710 is performed. This value indicates the minimum number of events that should occur between two events of the same subtype. Then a sort of rules by their sequence number (numbers that indicate a general order, the lower the number of the event means the more likely it will be seen first than other events with higher numbers) in ascending order in block 712 is performed. Finally, the system applies the first rule in the remaining set in block 714 from the rules sorted in blocks 708-712 according to the priority they have been given.

After the system chooses the next rule to apply, the system uses it to determine the next event to apply. Depending on the rule chosen, the system will go through the Events Database (112), match information from the User Demographic Database (108) and the User Cognitive Database (116), and sort through the events several times before picking the appropriate events. These steps are further described below.

Figure 8:
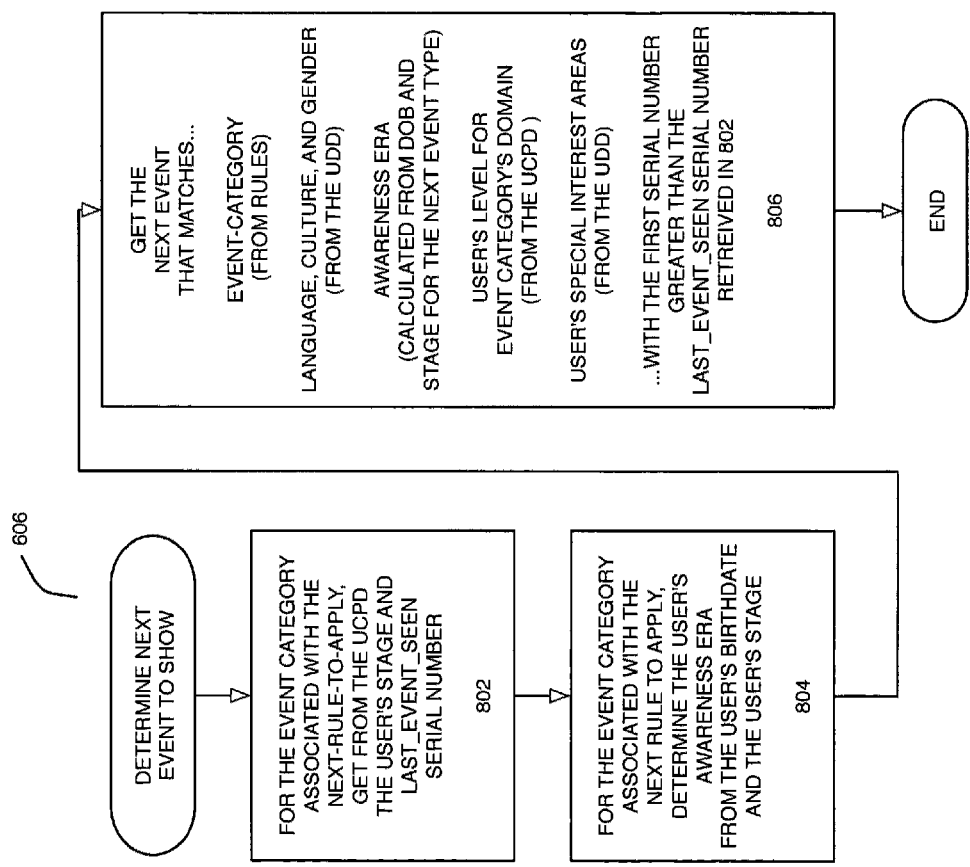
FIG. 8 is a flow chart illustrating the determination of the next event to apply, in accordance with an embodiment of the present invention.

Determining the Next Event to Apply (Step 606, FIG. 8)

To further explain the Next Event to Apply, reference is made to FIG. 8 which outlines the steps taken in step 606, "Determine Next Event to Apply." With further reference to FIG. 10, determining the Next Event to Apply would take place before each event that is between FIG. 10G and FIG. 10H, between FIG. 10J and FIG. 10K, between FIG. 10L and FIG. 10M, between FIG. 10S and FIG. 10T, between FIG. 10X and FIG. 10Y and between FIG. 10Y and FIG. 10Z, for example. Depending on the rule determined in the step above, the system may determine the next event in varying ways, but each follows the same basic steps. In block 802, for the event category associated with the next rule to apply determined previously, the system retrieves from the User Cognitive Profile Database (116) the user's current cognitive stage, that is, the present level of the user's cognitive ability and "Last Event Seen serial number." This "Last Event Seen serial number" is the term that is used for the last event the user has seen, to track the user's progress and to ensure variability of the events the user sees to avoid repetitiveness.

As the user uses the system and interacts with the events, the last event the user has seen is noted in the User Cognitive Profile Database (116), which is termed the "Last Event Seen serial number." Next, for the event category associated with the next rule to apply, the system determines the user's awareness era from the user's birth date plus ten years through the current date and the user's cognitive stage, in block 804. Depending on the Mental Status of the user, it may vary, typically decreasing at higher stages. At Stage 1, it may begin at the user's date of birth plus 15 years, ending at the present day. Stage 2 it may begin at user's date-of-birth plus 15 years and end 40 yrs later (age 55). At stage 3 it may begin at user's date-of-birth plus 15 yrs and end 20 yrs later (age 35). At stage 4 it may begin at user's date-of-birth plus 15 yrs and end 10 yrs later (age 25). Finally, with step 806 the system gets the next event that matches: the event category determined associated with the determined rule; the language, culture, and gender of the user retrieved from the User Demographic Database (108); the awareness era (previously calculated); the user's level for the event category's domain (retrieved from the User Cognitive Profile Database (116)); the user's special interest areas retrieved from the User Demographic Database (108); with the first serial number greater than the high-watermark serial number retrieved in step 802. Once the system finds the Next Event to Apply, the system presents the event to the user at the user's level in the particular event's domain.

Evaluation of User Responses and Adjustment of Difficulty Level, if Appropriate (Step 610)

To be effective, a cognitive stimulation system presents users with an optimum level of challenge. This is true for the following reasons: if the challenge is too great, the user will experience frustration; if the system is not challenging enough, the user will be bored. In either case, the user will likely lose interest in using the system—and therefore no longer receive the benefits of mental stimulation the system provides.

The system self-adjusts to provide users with the optimum level of challenge, as follows: As the user plays the system, it evaluates the user's responses to questions. Based on how many incorrect responses the user makes before choosing the correct response, the system determines if the difficulty level is too high or low for the user, and adjusts accordingly. This enables the system to customize the stimulation to the user's individual level of cognitive ability, mitigating the risks of user frustration and boredom.

The system self-adjusts independently for each user in each cognitive domain. This reflects the fact that cognitive functioning varies across domains for each individual, and that cognitive decline may take place at varying rates within each domain. With independent self-adjustment in each domain, each user can be at a different difficulty level in each domain, and the user's level in each domain can change independently, further mitigating the risks of user frustration and boredom.

There are specific criteria for the system to change the user's level in a domain. These are outlined in FIG. 11 and explained below. Each time a user responds to a given screen, this procedure starts at block 1102 and goes through a series of queries to see whether it's appropriate to adjust the user's difficulty level. Block 1102 evaluates results for a given screen and adjust the user's stage (user's cognitive level), if appropriate.

Increasing the Difficulty Level in a Domain

Figure 11:
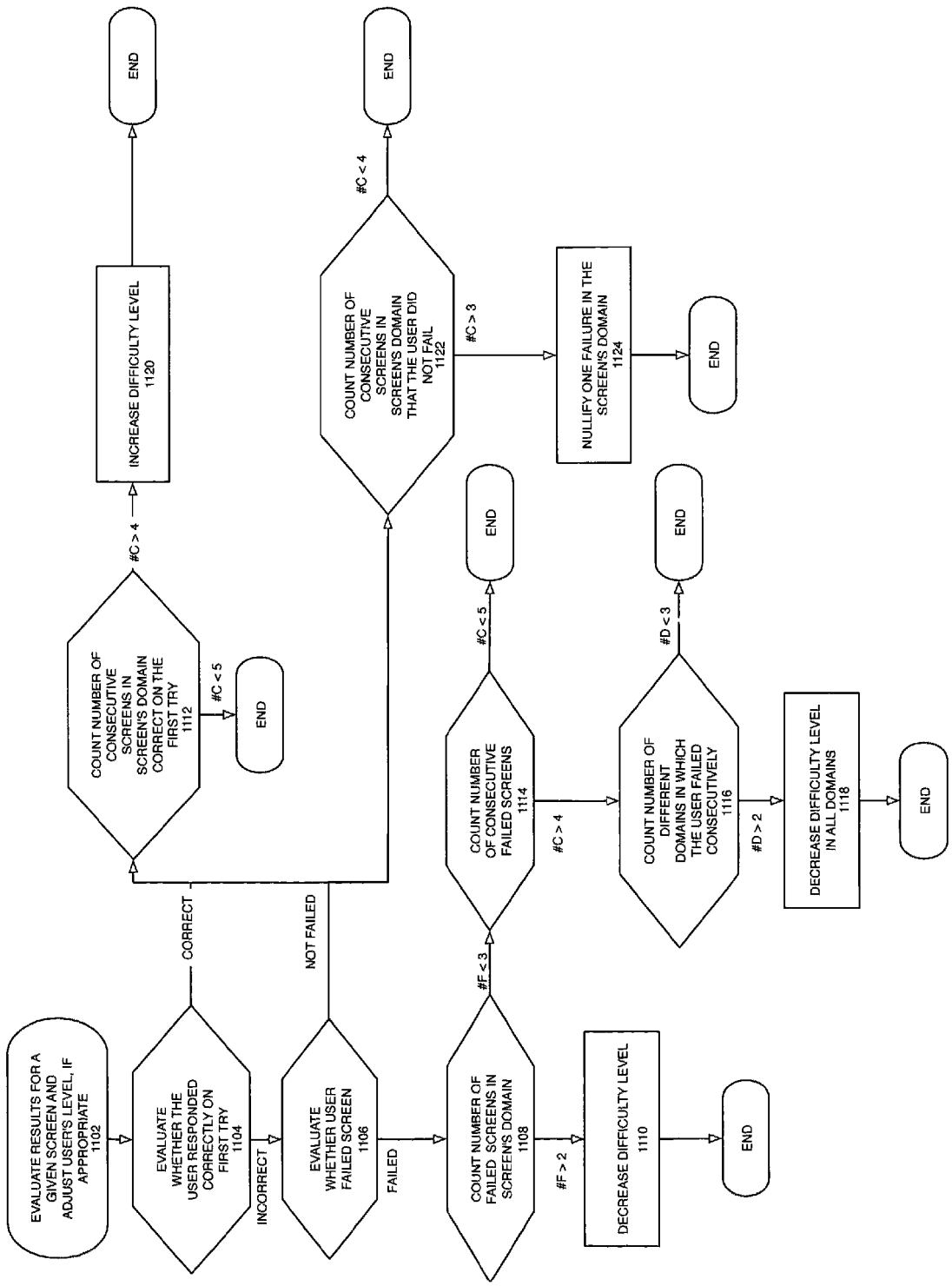
FIG. 11 is a flow chart illustrating the adjustment of the user's cognitive ability in a cognitive domain, in accordance with an embodiment of the present invention.

If, in one domain, the user answers a selected number of questions in a row correctly (five questions, for example) on the first attempt, the user will subsequently see more difficult content in that domain. Of course, the presentation of more difficult content is not to be perceived as a penalty, but rather a further challenge to enhance thought process and a feeling of accomplishment and reward for the user. This also indicates competency and/or sufficiency of cognitive ability. In FIG. 11, block 1104, the system evaluates whether the user had responded correctly on the first attempt. If so, the system in block 1112, continues to count the number of consecutive screens in the screen's domain where the user had responded correctly on the first attempt. If that number is below selected number, typically five, the process ends. If however the number is above another selected number, typically four, the system continues to block 1120 and raises the difficulty level. If the user does not answer correctly on the first attempt, the system will continue to block 1106 and evaluate whether the user had "failed" the screen.

Decreasing the Difficulty Level in a Domain

Two situations will cause the system to show easier content to the user. Both rely on the concept of a failed screen, indicative of a user's failure to successfully select the "correct" response in the manner described below.

Screen Failure (Block 1106)

A screen is considered failed if it exhibits the following combinations of screen attributes and user responses. If the screen is considered failed in any of the following cases, the system will continue to block 1108 and count the number of failed screens in that screen's domain:

1) The screen has only one correct response and the user makes at least two incorrect responses before arriving at the correct response.

2) The screen has multiple correct responses that do not have a specific sequence order and the user's number of incorrect responses before choosing all the correct responses is greater than or equal to two-thirds of the number of incorrect responses on the screen.

3) The screen has multiple correct responses that do have a specific sequence order and does not have buttons that are not in the sequence, and the user's number of out-of-sequence responses before arriving at the correct sequence is greater than or equal to two-thirds of the number of buttons on the screen.

4) The screen has multiple correct responses that do have a specific sequence order, does have buttons that are not in the sequence, and does not display a virtual keyboard or in the instance that the user's number of incorrect or out-of-sequence responses, before arriving at the correct sequence, is greater than or equal a predetermined percentage (preferably two-thirds) of the number of buttons on the screen. However, each response that is correct but out of sequence is multiplied by a predetermined percentage (preferably one-half) before beginning this calculation.

5) The screen displays a virtual keyboard; the user is required to spell a word that is the correct response, and the user has spelled at least two incorrect words before arriving at the correct word.

Decreasing the Difficulty in One Domain

The first situation that results in decreased difficulty of content seen by the user decreases the difficulty level in only one domain. The system will show easier content in a domain if the user has failed three screens in the domain. Experience has shown that three screen failures is the threshold for frustration in most users and the point at which users want to see easier content. In FIG. 11 block 1108, if the number of failed screens is above 2, the system moves on to block 1110 and decreases the difficulty level in that one domain.

No Screen Failure

If however none of the situations apply and there is no screen failure, the system moves to block 1122. It would be not be appropriate for the system to decrease the difficulty level of content merely because the user had simply been careless on a few screens, or had difficulty with one isolated subject in the domain, that is, if the user's three failed screens were an anomaly. To account for this possibility, the system provides a way to nullify failed screens. If the user does not fail on four consecutive screens in a domain, the system subtracts one from the number of screen failures in the domain seen in block 1124. The logic behind this is that, if a failure is truly an anomaly, then the user must prove this by performing above the failure threshold on multiple screens in succession. Otherwise, the process ends. The system also contemplates a special case where in the event an adjustment has been made by way of improvement from L4 or L5 and a single screen failure within the next three screen in the applicable domain occurs, the user will immediately returned from L3 to L4 or from L4 to L5 as the case may be. The rationale for the readjustment is to ensure that a user who should realistically be at L4 or L5 but who responds correctly and consecutively to several queries in L4 or L5, isn't elevated to L3 or L4 as the case may be, and left there inappropriately, but is quickly returned to the easier level (L's) after rapid subsequent failures.

Decreasing the Difficulty in all Domains

To account for the instance when three consecutive screen failures in one domain are followed by three failures in subsequent consecutive domains potentially resulting in 18 consecutive screen failures over six domains, the system has an override feature that will drop the difficulty level in all domains if the user has failed at least five screens in a row across at least three domains. Such a pattern of failures indicates the user is having a multi-domain decrement in functioning. This may be the result of the normal day-to-day fluctuation in mental acuity frequently seen in demented users, or it may be the result of a more serious medical problem, such as a small stroke. In either case, the system will accommodate the user by decreasing the difficulty level of all content shown to the user. Accordingly, the system in block 1108 counts the number of failed screens and if greater than three, the system moves to block 1114 and counts the number of consecutive failed screens. If the number of failed screens is below five, the difficulty level remains unchanged. If instead the number is above 4, then the system counts the number of different domains in which the user failed consecutively in block 1116. If the number of failed domains is less than three, the difficulty level remains unchanged. If however the number is above 2, then the system decreases the difficulty level in all domains in block 1118.

Interface Design, Apparatus and System

As mentioned above the device uses a touch screen interface 126A to overcome any technological barrier the user may have. The interface 126A may also include a camera 131 used at least for identifying the user. The events have a button/answer/input control that will either: disappear when a "correct" choice is made; use pictures, words, or numbers to display choices; and other possible mediums to interact with the user. This on-screen control can display further answers, and serve as an input device for user responses. The screen can also display an on-screen calendar for date orientation. Audio interface may be provided by a standard speaker 126B with accompanying electronics 950.

Figure 9:
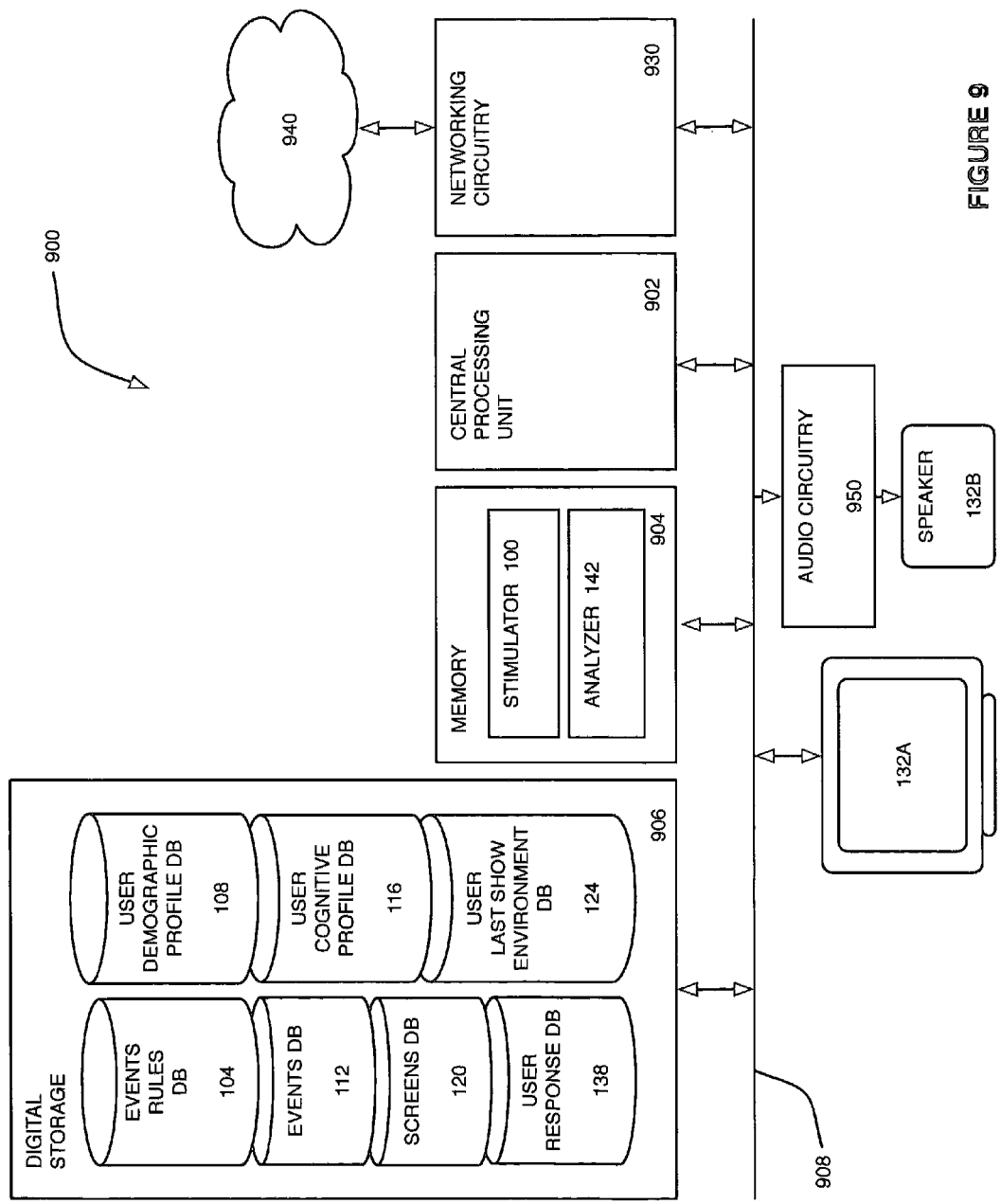
FIG. 9 is an illustration of a block diagram of system hardware components in accordance with an embodiment of the present invention; in accordance with an embodiment of the present invention.

As described for FIG. 1 and in further detail in FIG. 9, the device is composed of integrated hardware and software. The events rules data base 104, the events data base 112, the screens data base 120, the user response data base 138, the user demographic profile data base 108, the user cognitive data base 116 and the user last show environment data base 124 may be contained in a commercially available digital storage medium. The stimulator 100 and analyzer 142 may be implemented in memory units known to those skilled in the art. As described above, through an Internet connection the system through networking circuitry 930, can update or download content and upload user performance. Complex data manipulation and control processes may be undertaken in commercially available or specially designed central processing units 902. Also the device can provide reports and any important alerts regarding the user's performance to caregivers, physicians and family members. The device can be set up to function in a user's home, medical facility, senior care community, community center, therapeutic center, senior day care center and any similar area.

The descriptions of the invention, the specific details, and the drawings mentioned above, are not meant to limit the scope of the present invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes, which come within the meaning and range of equivalency of the claims, are to be embraced within their scope.

What is claimed is:

1. A system for providing adaptive rule based cognitive stimulation to a user during a stimulation session for mitigating the decline of and maintaining and improving a user's cognitive abilities, said user having an initial predetermined cognitive profile defined for a plurality of cognitive domains, said stimulation session comprising at least one event, said event contained within an event subtype, said event subtype contained within an event type, said event type contained within a cognitive domain, the system comprising:

a stimulator configured for providing interactive adaptive rule based cognitive stimulation to the user during a stimulation session of the user, wherein said stimulator is configured to:
  select an event type, an event subtype and an event in accordance with a plurality of predefined rules in an initial hierarchy of rules;
  establish a stimulation protocol in at least one cognitive domain based upon the hierarchy of predefined rules and the user's cognitive profile; and
  present cognitive stimulation in accordance with the stimulation protocol to the user via an interactive audio/visual display unit for user interaction therewith for mitigating the decline of and maintaining and improving the user's cognitive abilities;

an evaluator adapted to evaluate the user's responses to said cognitive stimulation and to provide user feedback indicative of the evaluated response, said evaluator further configured to:
  adaptively modify the user's cognitive profile as a function of the users evaluated response;
  adaptively modify the hierarchy of rules as a function of the user's modified cognitive profile; and
  establish a modified stimulation protocol based upon the modified hierarchy of rules and the modified user's cognitive profile prior to the presentation of a succeeding cognitive stimulation; and an audio/visual interactive display unit in communication with said stimulator, adapted for presenting cognitive stimulation to and receiving responses from said user.

2. The system of claim 1 wherein said stimulator establishes an initial cognitive ability of the user and a corresponding initial level of cognitive stimulation difficulty.

3. The system of claim 2 wherein the stimulator comprises means for utilizing demographic information comprising the user's birth date, gender, language, culture, education, profession, and personal preferences, said means further utilizing the user's cognitive information comprising short term memory, long term memory, calculation, visuospatial and critical thinking to establish the user's initial cognitive ability.

4. The system of claim 2 wherein cognitive stimulation comprises queries presented to the user via the audio/visual interactive display unit wherein the evaluator is configured to adjust the level of difficulty of subsequent queries in a selected cognitive domain as a function of the number and sequence of correct responses to prior queries in such selected cognitive domain.

5. The system of claim 4 wherein the evaluator is configured to adjust the user's cognitive profile in a selected cognitive domain as a function of the number and sequence of correct responses to prior queries in such selected cognitive domain.

6. The system of claim 4 wherein the evaluator is configured to utilize the hierarchy of rules to adjust the level of difficulty of the queries and the order of presentation of such queries in accordance with the user's adjusted cognitive profile.

7. The system of claim 4 wherein the evaluator is configured to provide congratulatory feedback to the user via said audio/visual interactive display unit upon receipt of a correct response and conciliatory positive reinforcement and encouragement upon receipt of an incorrect response in order to maintain and/or increase the user's self esteem and self confidence.

8. The system of claim 4 wherein the evaluator is configured to utilize a rule based protocol to adjust the level of difficulty of the queries and the order of presentation of such queries.

9. The system of claim 1 wherein, based upon user responses, the evaluator determines whether to increase, decrease or maintain a current level of event difficulty in a subsequent cognitive stimulation.

10. The system of claim 4 further comprising an analyzer configured to analyze a user's responses for indications of user health problems and to provide alerts upon indications of user health problems.

11. The system of claim 10 wherein the alerts provided by said analyzer comprise at least, communication to information recipients comprising the user, user caregivers, physicians and user friends and family.

* * * * *